US00PP33941P2

(12) United States Plant Patent
Growns

(10) Patent No.: US PP33,941 P2
(45) Date of Patent: Feb. 8, 2022

(54) ***GREVILLEA* PLANT NAMED 'KINGS SUNRISE'**

(50) Latin Name: ***Grevillea* hybrid**
Varietal Denomination: Kings Sunrise

(71) Applicant: Botanic Gardens and Parks Authority, Perth (AU)

(72) Inventor: Digby James Growns, Perth (AU)

(73) Assignee: BOTANIC GARDENS AND PARKS AUTHORITY, Perth (AU)

( * ) Notice: Subject to any disclaimer, the term of this patent is extended or adjusted under 35 U.S.C. 154(b) by 0 days.

(21) Appl. No.: 16/951,298

(22) Filed: Nov. 18, 2020

(51) Int. Cl.
*A01H 6/00* (2018.01)
*A01H 5/02* (2018.01)

(52) U.S. Cl.
USPC ..... Plt./226

(58) Field of Classification Search
USPC ..... Plt./226
CPC ..... A01H 6/00; A01H 5/00; A01H 5/02
See application file for complete search history.

(56) References Cited

U.S. PATENT DOCUMENTS

PP27,875 P3 4/2017 Growns

*Primary Examiner* — Keith O. Robinson
(74) *Attorney, Agent, or Firm* — Panitch Schwarze Belisario & Nadel LLP; Stephany G. Small; Travis W. Bliss

(57) ABSTRACT

A new and distinct variety of *Grevillea* plant, herein referred to by its cultivar name, 'Kings Sunrise', is provided which forms attractive orange colored flowers. Silvery-green colored foliage is formed. The vegetation is moderately vigorous, and the branching habit is freely branching. The new variety is particularly well suited for providing distinctive ornamentation in the landscape.

1 Drawing Sheet

Botanical/commercial classification:
Latin name: *Grevillea* hybrid.
Varietal denomination: 'Kings Sunrise'.

SUMMARY OF THE INVENTION

The new variety of *Grevillea* plant, botanically known as *Grevillea* hybrid, of the present invention originated by cross pollination in Perth, Western Australia, wherein two parents were crossed which previously had been studied in the hope that they would contribute the desired characteristics. The female parent (i.e., the seed parent) was the '20091434' variety (not patented). The male parent (i.e., the pollen parent) was the '20090089' variety (not patented).

The parentage can be summarized as follows:

'20091434' x '20090089'

The new cultivar was discovered and selected as a single flowering plant within the progeny of the above stated cross pollination during March 2012 in a controlled environment in Perth, Western Australia.

It was found that the new variety of *Grevillea* plant of the present invention possesses the following combination of characteristics:

(a) forms orange colored flowers,
(b) exhibits silvery-green colored foliage, and
(c) provides moderately vigorous vegetation.

The new variety well meets the needs of the horticultural industry. It can be grown to advantage as ornamentation in parks, gardens, public areas, and in residential settings. Accordingly, the plant is particularly well suited for growing in the landscape.

The new variety can be readily distinguished from its ancestors. More specifically, the '20091434' variety (i.e., the seed parent) displays red colored flowers and grey-green colored foliage and exhibits a low and spreading growth habit, whereas the new variety displays orange colored flowers and silvery-green colored foliage and exhibits a bushy shrub growth habit. The '20090089' variety (i.e., the pollen parent) displays yellow colored flowers and green colored foliage, whereas the new variety displays orange colored flowers and silvery-green colored foliage. Moreover, the new variety can be readily distinguished from other similar non-parental varieties. For example, the 'Kings Fire' variety (U.S. Plant Pat. No. 27,875) exhibits bright red colored flowers, whereas the new variety exhibits orange colored flowers.

The new variety has been found to undergo asexual propagation in Perth, Western Australia by terminal stem cuttings since March 2012. Asexual propagation by terminal stem cuttings in Perth, Western Australia has shown that the characteristics of the new variety are homogeneous, stable, and strictly transmissible by such asexual propagation from one generation to another. Accordingly, the new variety undergoes asexual propagation in a true-to-type manner.

The new variety has been named 'Kings Sunrise'.

BRIEF DESCRIPTION OF THE PHOTOGRAPHS

The accompanying photographs show, as nearly true as it is reasonably possible to make the same in color illustrations of this character, typical specimen of the new variety. Colors in the photographs differ slightly from the color designations cited in the detailed description, which accurately describes the colors of the new variety. The illustrated specimen was grown in a three-gallon container for two years in an outdoor nursery in Valley Center, Calif. and was photographed in December, 2019.

Drawing—illustrates specimens of the inflorescence in the course of opening—close-up view.

DETAILED BOTANICAL DESCRIPTION

The chart used in the identification of colors described herein is that of The Royal Horticultural Society (R.H.S. Colour Chart) London, England, 1995 edition, except where general color terms of ordinary significance are used. The terminally which precedes reference to the chart has been added to indicate the corresponding color in more common terms. The color values were determined in April 2021 under natural light conditions in Valley Center, Calif.

The following descriptions and measurements describe plants produced from cuttings from stock plants. The plants were grown in 5-gallon containers for four years in an outdoor nursery in Valley Center, Calif. Measurements and numerical values represent averages of typical plants.

Botanical classification: *Grevillea* hybrid 'Kings Sunrise'.

Parentage:

*Female parent*.—Proprietary breeding seedling, *Grevillea* 20091434, not patented.

*Male parent*.—Proprietary breeding seedling, *Grevillea* 20090089, not patented.

Propagation:

*Type cutting*.—Terminal stem cuttings.

*Time to initiate roots*.—Approximately 14 to 16 weeks.

*Time to produce a rooted cutting*.—Approximately 22 to 26 weeks.

*Root description*.—Light brown in color, fine.

*Rooting habit*.—Freely branching.

Plant:

*Growth habit and general appearance*.—Moderately vigorous.

*Size*.—Height from soil level to top of plant plane: Approximately 120.0 to 140.0 cm. — Width: Approximately 100.0 to 120.0 cm.

*Branching habit*.—Freely branching. Pinching enhances branching. — Quantity of branches per plant: Approximately 2 to 3. — Branch Strength: Strong. — Length to base of peduncle: Approximately 10.0 to 14.0 cm. — Diameter: Approximately 4.0 to 5.0 cm. — Length of central internode: Approximately 6.0 to 8.0 cm. — Texture: Tomentose. — Pubescence color: commonly near White Group 155C. — Color of young stems: commonly near Greyed-Green Group 190D. — Color of mature stems: commonly near Greyed-Green Group 196D.

Foliage:

*General description*.—Form: Simple. — Arrangement: Alternate. — Fragrance: None detected.

*Leaves*.—Aspect: Acute angle to stem. — Margin: Entire, pinnatisect. — Apex of lobes: Acute. — Base: Slender attenuate. — Venation pattern: Pinnate. — Length of mature leaf: Approximately 9.5 cm. — Width of mature leaf: Approximately 5.0 cm. — Texture of upper and lower surfaces: Tomentose. — Pubescence color: commonly near White Group 155C. — Color of upper surface of young foliage: commonly near Greyed-Green Group 194D. — Color of lower surface of young foliage: commonly near Greyed-Green Group 190D. — Color of upper surface of mature foliage: commonly near Greyed-Green Group 191B. — Color of lower surface of mature foliage: commonly near Greyed-Green Group 194B.

Flower:

*Flowering habit*.—Freely flowering habit under outdoor growing conditions with substantially continuous blooming in Zone 8 through 11.

*Lastingness of individual inflorescence on the plant*.—Approximately 3 weeks.

Inflorescence description:

*General description*.—Type: Raceme. Self-cleaning. — Shape: Tubular. — Aspect: Facing upwards. — Arrangement: Terminal and from leaf axils. — Fragrance: none detected. — Quantity per plant: Approximately 15 to 20. — Inflorescence Diameter: Approximately: 3.0 cm. — Depth: Approximately 10.0 cm.

*Bud*.—Rate of opening: Generally, takes 6 to 8 days for bud to progress from first color to fully open floret.

*Bud just before opening*.—Shape: Globular. — Diameter: Approximately 1.0 to 1.5 mm. — Texture of outer surface: Tomentose. — Pubescence color: commonly near Yellow-Green Group 150D. — Color: commonly near Greyed-Green Group 191D.

*Florets*.—Quantity per inflorescence: Approximately 84-112. — Arrangement: Primarily in pairs. — Length: Approximately 6.0 to 8.0 mm. — Diameter: Approximately 2.0 to 2.5 mm.

*Perianth*.—Shape: Tubular with a ventral limb. — Length: Approximately 4.0 mm. — Diameter at widest point: Approximately 2.0 to 3.0 mm. — Diameter as base: Approximately 1.0 to 2.0 mm.

*Tepals*.—Quantity: 1. — Shape: Linear. — Margin: Entire. — Apex: Acute. — Length: Approximately 1.0 mm. — Width: Approximately 3.0 mm. — Texture of outer and inner surfaces: Smooth. — Color of outer surface when fully open: commonly near Orange-Red Group 31B. — Color of inner surface when fully open: commonly near Orange-Red Group 30A.

*Peduncle*.—Strength: Strong. — Aspect: Erect. — Length: Approximately 3.0 to 6.0 mm. — Diameter: Approximately 2.0 to 3.0 mm. — Texture: Tomentose. — Color: commonly near Yellow-Green Group 145C.

*Rachis*.—Strength: Strong. — Length: Approximately 10.0 to 12.0 cm. — Diameter: Approximately 2.0 to 3.0 cm. — Texture of outer surface: Tomentose. — Pubescence color: commonly near Greyed-White Group 156D.

*Pedicel*.—Strength: Strong. — Aspect: Erect. — Length: Approximately 1.0 to 2.0 mm. — Diameter: Approximately 2.0 mm. — Texture of outer surface: Tomentose. — Pubescence color: commonly near Greyed-White Group 156D. — Color: commonly near Yellow-Green Group 145B.

*Reproductive organs*.—Androecium: Anthers located within perianth limb and basally attached to perianth. — Anther quantity: 1 per floret. — Anther Shape: Bilobed. — Anther length: Approximately 1.0 mm. — Anther color: commonly near Yellow-Orange Group 20B. — Pollen amount: Slight. — Pollen color: commonly near Orange Group N25D. — Gynoecium: Stigma functions as a pollen presenter holding pollen for pollinators to remove until stigma matures becoming receptive to cross pollination. Nectary located at base of ovary. — Pistil quantity: 1 per flower. — Pistil length: Approximately 4.0 to 5.0 cm. — Stigma shape: Oval. — Stigma length: 1.0 mm. — Stigma color: commonly near Orange Group N25A. — Style length: Approximately 23.0 to 4.0 cm. — Style color: commonly near Yellow-Orange Group 20B. — Ovary length: Less than 1.0 mm. — Ovary texture: Tomentose. — Ovary Pubescence color: commonly near Yellow-White Group 158C. — Ovary color: commonly near Green-White Group 157B. — Nectary size: Approximately 1.5 mm in length and 1.0 mm in width. — Nectary color: commonly near Yellow Group 10D.

*Seed and fruit production*.—Neither seed nor fruit production has been observed.

Development:

*Disease and pest resistance*.—Resistance to pathogens and pests common to *Grevillea* has not been observed.

*Commercial crop time*.—Approximately 20 to 24 weeks from a rooted cutting to finish in a one-gallon container.

*Hardiness*.—USDA Zone 8 through 11.

Plants of the 'Kings Sunrise' variety have not been observed under all possible environmental conditions to date. Accordingly, it is possible that the phenotypic expression may vary somewhat with changes in light intensity and duration, cultural practices, and other environmental conditions, without, however, any variance in genotype.

I claim:

1. A new and distinct *Grevillea* plant named 'Kings Sunrise' characterized by the following combination of characteristics:

(a) forms orange colored flowers, (b) exhibits silvery-green colored foliage, and (c) provides moderately vigorous vegetation;

substantially as herein shown and described.

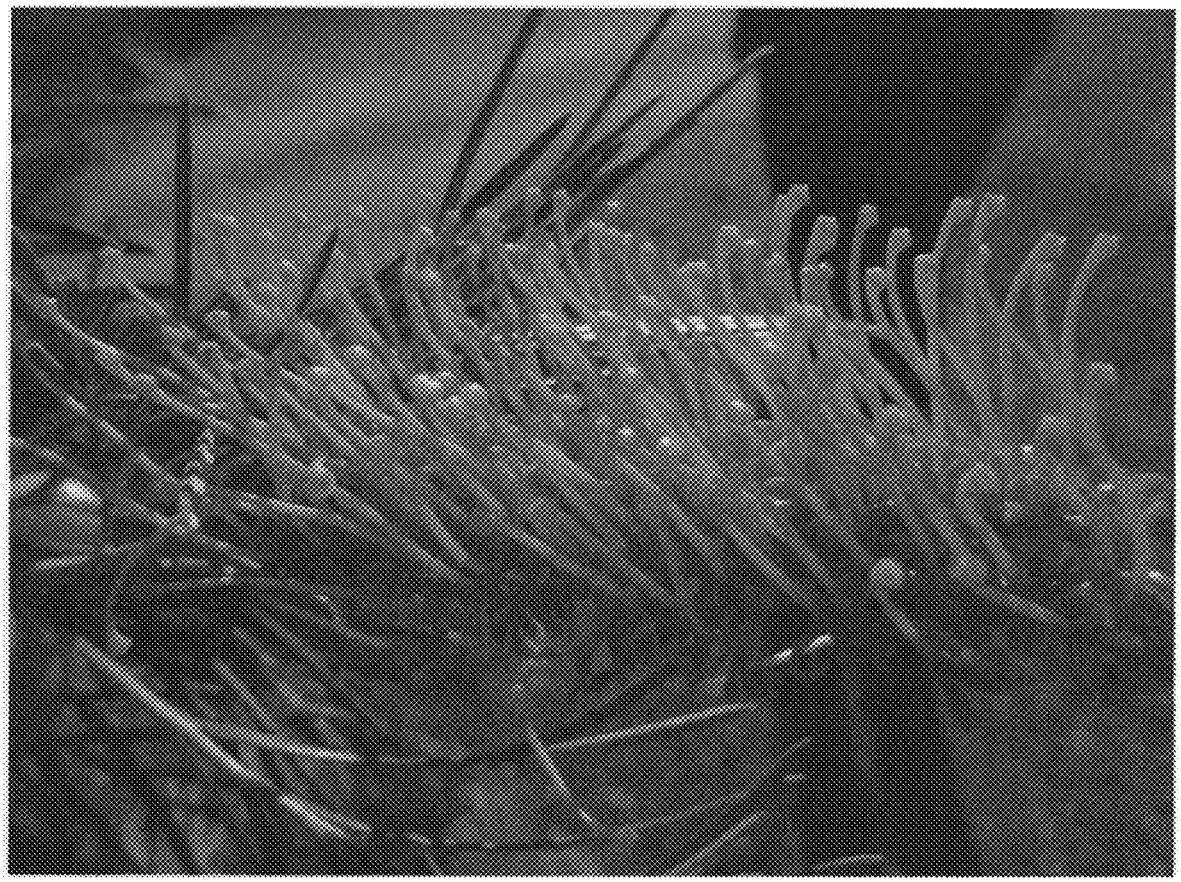

* * * * *